United States Patent [19]

Bechgaard et al.

[11] 4,193,985
[45] Mar. 18, 1980

[54] MULTIPLE-UNITS DRUG DOSE

[75] Inventors: Helle Bechgaard, Hellerup; Arne M. Pedersen, Vanlose, both of Denmark

[73] Assignee: A/S Alfred Benzon, Copenhagen, Denmark

[21] Appl. No.: 889,269

[22] Filed: Mar. 23, 1978

[30] Foreign Application Priority Data

Mar. 30, 1977 [GB] United Kingdom ............... 13296/77

[51] Int. Cl.² .......................... A61K 9/22; A61K 9/54
[52] U.S. Cl. ......................................... 424/19; 424/24; 424/14; 424/16; 424/20; 424/32; 424/33; 424/35
[58] Field of Search ................. 424/24, 14, 16, 19–22, 424/32, 33, 35

[56] References Cited

U.S. PATENT DOCUMENTS

| | | | |
|---|---|---|---|
| 2,801,203 | 7/1957 | Leb et al. | 424/4 |
| 3,017,329 | 1/1962 | Dulmage | 424/4 |
| 3,056,724 | 10/1962 | Marston | 424/22 |
| 3,341,417 | 9/1967 | Sinaiko | 424/4 |
| 3,368,944 | 2/1968 | Sandmark et al. | 424/4 |
| 3,444,290 | 5/1969 | Wai | 424/4 |
| 3,592,185 | 7/1971 | Frei et al. | 424/158 X |
| 3,608,061 | 9/1971 | McNally | 424/4 |
| 3,775,537 | 11/1973 | Lehmann et al. | 424/21 |
| 3,917,813 | 11/1975 | Pedersen | 424/35 X |

FOREIGN PATENT DOCUMENTS

| | | | |
|---|---|---|---|
| 42-25410 | 12/1967 | Japan | 424/4 |
| 42-25412 | 12/1967 | Japan | 424/4 |
| 41-10798 | 5/1969 | Japan | 424/4 |
| 41-10799 | 5/1969 | Japan | 424/4 |
| 44-27839 | 11/1969 | Japan | 424/4 |
| 48-24246 | 7/1973 | Japan | 424/4 |

*Primary Examiner*—Shep K. Rose
*Attorney, Agent, or Firm*—Merriam, Marshall & Bicknell

[57] ABSTRACT

A controlled release multiple-units drug dose is described, which comprises a tablet or a capsule enclosing a plurality of subunits, each containing a therapeutically active agent and being enclosed in an insoluble membrane allowing for diffusion of the juices of the gastrointestinal tract, at least some of the subunits being of increased specific weight as compared with the specific weight of the active agent.

4 Claims, No Drawings

MULTIPLE-UNITS DRUG DOSE

This invention relates to oral drug depot formulations of the multi-units type with a controlled release action of short or long duration of the active agent or agents. A multiple-units dose consists of a great number of subunits, usually in the form of pellets or microencapsulated crystals contained in a capsule or tablet.

Oral depot products can be formulated according to two different principles: The controlled release single-unit dose or the multiple-units dose.

A single-unit dose, e.g. a matrix tablet or a tablet enclosed in a diffusion membrane, is a depot which releases a drug during the passage of the entire alimentary canal without disintegrating. The empty core or shell is discharged.

A multiple-unit dose consists of a large number of mini-depots, e.g. pellets or microencapsulated crystals, contained in a capsule or a tablet. These many subunits are dispersed and distributed throughout the gastrointestinal tract when the capsule or tablet disintegrates.

An adjustment of the release rate of the depot according to its transit time through the small intestine is essential to the achievement of a satisfactory bioavailability, as the greatest absorption capacity is generally possessed by this part of the gastrointestinal tract, particularly the jejunum and the proximal ileum.

Single-unit doses tend to follow the food having a normal transit time through the small intestine that varies between 3 and 8 hours. Accordingly, 6-10 hours are recommended by many authors as the maximum duration of in vitro release from depot formulations.

In some cases it is desirable, however, to retain the drug depot in the upper gut in order (i) to assure optimal absorption or (ii) to additionally extend the absorption phase. The latter applies e.g. to drugs with biological half-lives requiring an absorption period of more than 6-10 hours to facilitate a lower dosage frequency (once daily) and thus a more secure therapy.

As the subunits of the multiple-units formulations are distributed freely throughout the gastrointestinal tract, their transport is to a greater extent independent of the transit time of food. Hence the bioavailability of these products is less vulnerable to variations in both gastric emptying and intestinal transit time, providing a more secure interaction between in vitro release and bioavailability and thus a better reproducible effect.

Accordingly, the multiple-units dose principle is expected to facilitate the production of drug depots with a reproducible and predetermined prolonged intestinal transit time.

Obviously, it would be advantageous if the absorption period could be extended in order to reduce the frequency of drug administration to, for example, once daily, thus improving patient compliance and reducing the risk of erroneous administration.

The invention is based upon the observation that the specific weight of the subunits in a multiple-units dose greatly influences the average transit time of the subunits through the gastrointestinal tract.

A pilot study showed that in the same patient an increase by 0.6 g/ml in the specific weight of the subunits (pellets or microencapsulated crystals) in a multiple-units dose increased the transit time of the subunits through the gastrointestinal tract up to 5 times, irrespectively of the size of the subunits.

An object of the invention is thus to utilize this discovery to obtain a reproducible, prolonged transit time, through the gastrointestinal tract, of the subunits of a multiple-units dose.

According to the invention, therefore, a controlled-release multiple-units drug dose comprises a tablet or capsule enclosing encapsulated pellets, granules or crystals of a therapeutically active agent, the specific weight of at least some of which has been increased to a specific weight of at least 1.4 by means of a physiologically inert or innocuous substance of higher specific weight than that of the therapeutically active agent.

The said increase of the specific weight ensures that the units get a specific weight exceeding that of the normal gut contents.

The increase can be attained e.g. by incorporating the physiologically inert or innocuous substance in the core or the coating material of the pellets or the coating material of the microencapsulated crystals, or in any other known way.

Examples of substances, which can be used to increase the specific weight of the subunits in a controlled-release multiple-units dose, are barium sulphate, zinc oxide, titanium dioxide, and iron powder produced by reduction (ferrum reductum).

The use of a controlled-release multiple-units dose is also advantageous because dispersal of the subunits along the gastrointestinal tract results in lower local concentration of the active substance, thus causing less irritation of the mucosa in case of irritative drugs.

Since a greater specific weight tends to increase the transit time of the subunits, obviously a combination of lighter and heavier subunits in a multiple-units dose has the effect of further dispersing the units along the gastrointestinal tract. Mixing of subunits of different specific weight and/or with different active agents could also be advantageous in the formulation of a controlled-release multiple-units combined product.

The controlled, prolonged drug release means also that unnecessary peak concentrations in the blood with their inherent risks of exaggerated drug action or enhanced side effects of both are avoided and that adequate treatment over extended time periods is ensured.

Clinical investigations have shown that the transit time of the individual units of a multiple-units dose can easily be extended over a 24 hours period by suitably increasing the specific weight of the subunits.

Thus, according to the invention, a substantial proportion, e.g. at least 5% and preferably at least 20%, and sometimes at least 50%, by weight of the total composition is in the form of subunits having specific weight greater than the specific weight of the entire drug composition. The amount by which the specific weight of some of the subunits is above the average can vary widely, but preferably it is at least 5% above the average and preferably at least 20%. Expressed in another way at least 25% by weight of the subunits preferably have a specific weight at least 25% above the specific weight of other subunits in the composition.

Although the drug release from the subunits of the multiple-units dose can be controlled in various known ways, the preferred manner of controlling is by coating the subunits with a diffusion membrane which is insoluble in and not degradable by the gastrointestinal juices.

The subunits can be composed as follows. An inactive, heavy core can be provided with a layer of the active agent by means of a suitable adhesive, and then provided with a diffusion membrane.

Alternatively, the active agent can be mixed with the innocuous heavy substance, the mixture being formed to pellets or granules, and coated with the diffusion membrane.

A third possibility is using crystals of the active agents as cores in the subunits.

In all cases, the amount and specific weight of the inactive substance determines the increase in specific weight of the subunits.

A pilot study was aimed at observing the influence on transit time of variations in specific weight and size of the subunits. Four ileo-colostomy patients, three females and one male, aged between 24 to 40 years, three with part of the small intestine resected, volunteered for the study. The post-operative period was from 2 to 6 months. As determined the day before the investigation, each patient had a gastrointestinal transit time of at least 2½ hours.

Coated pellets were used, prepared either with barium sulphate (specific weight of pellets 1.6 g/ml) or with paraffin wax (specific weight of pellets 1.0 g/ml). In both cases, the diameters were 0.3–0.7 mm and 1.2–1.7 mm, respectively.

After a 12 hours fasting period, a transparent colostomy bag was fitted to the patient, and 1850 pellets suspended in a standard meal were administered. After this meal, the patients resumed the usual hospital meal routine.

The investigation period was 36 hours. During the first 12 hours, the colostomy bag was totally emptied every 3 hours, during the next 12 hours intermittently as needed, and during the final 12 hours again every 3 hours.

The contents from each emptying were investigated separately, counting the contents of the four different types of pellets to determine the transit time.

The following tables illustrate the results of the investigations.

Table 1

| Number, size, and specific weight of the pellets | | | |
|---|---|---|---|
| Number of pellets | Diameter | | |
| | 0.3–0.7 mm | 1.2–1.7 mm | Total |
| Light pellets sp.w. 1.0 g/ml | 800 | 125 | 925 |
| Heavy pellets sp.w. 1.6 g/ml | 800 | 125 | 925 |
| | 1600 | 250 | 1850 |

Table 2

| Recovery of pellets | | | |
|---|---|---|---|
| | | Diameter | |
| Patient | Sp. weight | 0.3–0.7 mm | 1.2–1.7 mm |
| EBO | 1.0 | 87.9% | 98.4% |
| | 1.6 | 95.6% | 96.0% |
| IMC | 1.0 | 88.9% | 95.2% |
| | 1.6 | 64.9% | 64.8% |
| MH | 1.0 | 76.1% | 67.2% |
| | 1.6 | 71.3% | 41.6% |
| PKB | 1.0 | 89.8% | 95.2% |
| | 1.6 | 72.5% | 77.6% |

Table 3

| Average transit time for pellets in hours | | | | | | | | |
|---|---|---|---|---|---|---|---|---|
| | | EBO | | IMC | | MH | | PKB[1] |
| Sp.w. | Diam. | 0.3–0.7 | 1.2–1.7 | 0.3–0.7 | 1.2–1.7 | 0.3–0.7 | 1.2–1.7 | 0.3–0.7 | 1.2–1.7 |
| 1.0 | | 3.2 | 1.8 | 6.5 | 7.9 | 12.9 | 16.9 | 9.0 | 9.8 |
| 1.6 | | 13.5 | 9.5 | 23.7 | 27.3 | 16.0 | 19.3 | 10.7 | 10.1 |

[1] One colostomy bag was lost during the 5th interval of the investigation period. The number of each type of pellets in the lost bag has been calculated on the assumption that the probability of recovery would be equal to that of EBO.

The extension of the transit time attained by an increase of the specific weight of the pellets is clearly demonstrated by Table 3.

Continued clinical investigations comprised six ileo-colostomy out-patients, five females and one male, aged between 25 and 50 years. Two of the patients had part of the ileum resected.

Participation in the study was conditional upon the patient having terminated a post-operative period of 2 months and having a transit time at least 3 hours, as determined on the day before the examination.

Coated pellets identical to those in the pilot study were used.

In the morning of the day of examination, the fasting (12 hours) ileo-colostomy patient had a transparent colostomy bag fitted, and at the same time 250 pellets of each of the four kinds, or a total of 1000 pellets, were administered, suspended in a standard meal.

After the test meal, the patient resumed the usual meal and locomotive routine. The colostomy bag was emptied completely every 2 hours during the first 14 hours, and then every 4 hours during the following 8 hours of night. The pattern of emptying was repeated the following day in order to complete a 48 hours' observation period.

The collected fractions were analysed by manually picking off the pellets from thin layers of the visceral contents.

The frequency of pellets in the colostomy bags during the first day, defined as the period from 8 a.m. to 2 a.m., is shown in Table 4. The difference in frequencies of the four types of pellets having passed the small intestine during the first day is seen to be caused mainly by the differences in specific weight of the pellets, the influence of the different diameters of pellets being less important.

Table 4

| Frequency (%)[1] of pellets during the first day of observation | | | | | | | | |
|---|---|---|---|---|---|---|---|---|
| Size mm | Specific weight | Patients | | | | | | Average |
| | | BMM | VN | AS[2] | HB | JPL | IO[3] | |
| 0.3–0.7 | 1.0 | 100.0 | 100.0 | 91.9 | 90.4 | 100.0 | 97.7 | 97.6 |
| | 1.6 | 17.2 | 6.3 | 77.0 | 9.8 | 16.4 | 16.6 | 13.3 |
| 1.2–1.7 | 1.0 | 99.1 | 99.6 | 99.2 | 77.2 | 96.8 | 87.6 | 92.1 |
| | 1.6 | 10.9 | 4.4 | 68.8 | 2.1 | 3.4 | 5.4 | 5.2 |

[1] Relative to recovered pellets. The average of recovered pellets of all four kinds in the total observation period was 90% (range 84–95%).
[2] The patient AS is atypical, owing to a very large consumption of liquid, totalling 5900 ml (thereof 5000 ml of beer), during the test period.
[3] The figures for the patient IO is the average of two replicate studies.

The figures shown that the specific weight is of significant importance ($p < 0.05$) for the prolongation of the transit time of the subunits, whereas it is doubtful whether an increase in size if of importance.

The following Examples illustrate different ways of preparing pellets with increased specific weights for use in controlled-release multiple-units doses.

EXAMPLE 1

The components of the core of a pellet are:

| | Parts by weight |
|---|---|
| Ferrum reductum | 80 |
| 4-(2-Hydroxy-3-isopropylaminopropoxy)-indole | 6 |
| Microcrystalline cellulose | 6 |
| Talcum | 2 |
| Hydroxypropylcellulose | 3 |
| Sodium hydrogen carbonate | 3 |

The components are mixed and moistened with 20 parts by weight of water, after which the mass is extruded to form strings of 1 mm diameter, from which balls of approximately 1 mm diameter are formed. After drying, the specific weight of the balls is 3.7.

The balls are coated with a solution of an acrylic polymer, marketed under the registered trade mark Eudragit RS, the specific weight being 3.4 after the coating.

EXAMPLE 2

The core components of a pellet are:

| | Parts by weight |
|---|---|
| Zinc oxide | 95 |
| Polyethylene powder | 5 |

The components are mixed, moistened with 16 parts by weight of water, and extruded to strings of 0.8 mm diameter, from which balls with about the same diameter are formed. After drying, the specific weight of the balls is 3.0.

The cores are then coated with 15 parts by weight of ethylphenylephrine hydrochloride (α-[(ethylamino)methyl]m-hydroxybenzyl alcohol hydrochloride) by alternatively moistening with a 3% solution of ethylcellulose in isopropanol and coating with the powdered drug.

Finally, an external coating is applied, consisting of ethylcellulose with 10% by weight of acetyltributyl citrate admixed as a softening agent.

The specific weight of the resulting pellets is 2.7.

EXAMPLE 3

The components of the subunits are:

| | Parts by weight |
|---|---|
| Acetylsalicylic acid crystals | 65 |
| Titanium dioxide | 32.5 |
| Acrylic polymer (Eudragit ® RS) | 2.5 |

In a coating pan, the crystals of acetylsalicylic acid (specific weight 1.37) are alternatively moistened with a 3% solution of the acrylic polymer, and dusted with titanium dioxide powder.

The specific weight of the resulting coated crystals is 1.6.

We claim:

1. A controlled release upper-gut retentive gastrointestinal tract transit time increasing multiple-units drug dose, which comprises a tablet or a capsule, enclosing subunits of a therapeutically active agent in the form of 0.3 to 1.7 millimeter balls or pellets, each of which are enclosed in an insoluble dialysis membrane of a cellulose ether or acrylic polymer allowing for diffusion of the juices of the gastrointestinal tract, the specific weight of at least 25% by weight of which subunits has been increased from 1.0 or less to at least 1.4 by means of a physiologically innocuous substance of higher specific weight than that of the therapeutically active agent.

2. A controlled release upper-gut retentive gastrointestinal tract transit time increasing multiple-units drug dose, which comprises a tablet or a capsule, enclosing subunits of a therapeutically active agent in the form of spherical 0.3 to 1.7 millimeter balls or pellets, each of which are enclosed in an insoluble dialysis membrane of ethyl cellulose or acrylic polymer allowing for diffusion of the juices of the gastrointestinal tract, the specific weight of at least 25% by weight of which subunits has been increased to at least 1.4 by means of barium sulfate, zinc oxide, titanium dioxide or ferrum reductum, as a physiologically innocuous substance of higher specific weight than that of the therapeutically active agent, and the other subunits in the drug dose have an otherwise unchanged specific weight of 1.0 or less.

3. A drug dose as set forth in claim 2, in which the specific weight of at least some of the subunits is at least 1.6.

4. A drug dose as set forth in claim 2, in which subunits of different specific weights contain different therapeutic agents.

* * * * *